United States Patent [19]

DeCarli et al.

[11] Patent Number: 5,262,945
[45] Date of Patent: Nov. 16, 1993

[54] METHOD FOR QUANTIFICATION OF BRAIN VOLUME FROM MAGNETIC RESONANCE IMAGES

[75] Inventors: Charles DeCarli, Germantown; Barry Horwitz, Gaithersburg, both of Md.

[73] Assignee: The United States of America as represented by the Department of Health and Human Services, Washington, D.C.

[21] Appl. No.: 742,763

[22] Filed: Aug. 9, 1991

[51] Int. Cl.[5] ............................................ G06F 15/42
[52] U.S. Cl. ................................................. 364/413.13
[58] Field of Search ............... 364/413.13, 413.14, 364/413.15, 564; 395/124, 142, 143; 382/51, 52, 54, 6, 18; 128/653.1, 653.2

[56] References Cited

U.S. PATENT DOCUMENTS

| | | | |
|---|---|---|---|
| 4,766,556 | 8/1988 | Arakawa | 395/124 |
| 4,977,505 | 12/1990 | Pelizzari et al. | 364/413.13 |
| 5,038,302 | 8/1991 | Kaufman | 395/124 |
| 5,099,846 | 3/1992 | Hardy | 364/413.13 |
| 5,107,838 | 4/1992 | Yamaguchi | 128/653.2 |
| 5,150,421 | 9/1992 | Morishita et al. | 382/6 |
| 5,166,875 | 11/1992 | Machida | 364/413.13 |
| 5,166,876 | 11/1992 | Cline et al. | 364/413.13 |

OTHER PUBLICATIONS

DeCarli et al., "Critical Analysis of the Use of Computer-Assisted Transverse Axial Tomography to Study Human Brain in Aging and Dementia of the Alzheimer Type", *Neurology*, vol. 40, (1990), pp. 872–883.

Kohn et al., "Analysis of Brain and Cerebrospinal Fluid Volumes with MR Imaging", *Radiology*, vol. 178, (1991), pp. 115–122.

DeLeo et al., "Computer-Assisted Categorization of Brain Computerized Tomography Pixels into Cerebrospinal Fluid, White Matter, and Gray Matter", *Computers and Biomedical Research*, vol. 18, (1985), pp. 79–88.

Davis et al., "A New Method for Measuring Cranial Cavity Volume and its Application to the Assessment of Cerebral Atophy at Autopsy", *Neuropathology and Applied Neurobiology*, vol. 3, (1977), pp. 341–358.

Miller et al., "Variation with Age in the Volumes of Grey and White Matter in the Cerebral Hemispheres of Man: Measurements with an Image Analyser", *Neuropathology and Applied Neurobiology*, vol. 6, (1980), pp. 119–132.

*Primary Examiner*—Donald E. McElheny, Jr.
*Attorney, Agent, or Firm*—Lowe, Price, LeBlanc & Becker

[57] ABSTRACT

A simple, rapid and semi-automated method of MRI analysis based on mathematical modelling of MRI pixel intensity histograms. The method is accurate and reliable for regional analysis of brain, central and subarachnoid CSF volumes. The method can be used to reveal significant age-related changes in regional brain volumes which cannot be determined utilizing traced central CSF volumes or subarachnoid CSF volumes. The method can be used to quantify brain structure in healthy aging and brain disease.

10 Claims, 5 Drawing Sheets

METHOD FOR QUANTIFICATION OF BRAIN VOLUME FROM MAGNETIC RESONANCE IMAGES

TECHNICAL FIELD

The present invention relates to methods of analyzing brain volumes. More particularly, the present invention relates to methods of analyzing and classifying brain volumes from magnetic resonance images.

BACKGROUND ART

Postmortem studies of the human brain reveal consistent age-related reductions in brain size and age-related increases in cerebro-spinal fluid spaces (CSF) which are accentuated in Alzheimer's disease. Previous studies utilizing quantitative X-ray computerized axial tomography (CT) have confirmed these postmortem findings in healthy controls free of obvious brain disease. Quantitative CT also has demonstrated significant, progressive increase in ventricular CSF size accompanying development of dementia of the Alzheimer type. Quantitative CT, however, has several limitations which prevent accurate determination of subarachnoid CSF and of temporal lobe volumes, such as bone hardening artifact and lack of high resolution coronal imaging.

Magnetic resonance imaging (MRI) offers high contrast images which are unimpaired by bone-hardening artifacts intrinsic to CT. In addition, flexible imaging sequences and choices of image orientation allow for detailed analysis of the temporal lobes, and for computer methods which can accurately segment the brain into CSF, gray matter and white matter compartments.

To date, a number of quantitative MRI methods have reported measurements of CSF, temporal lobe, gray and white matter volumes in brain. Three general methods have been employed: (1) operator directed outlining of a region of interest (ROI); (2) special sequences to enhance CSF and suppress brain matter signals; and (3) segmentation routines which utilize either automatic boundary outlining or threshold determinations.

Although tracing a ROI can be quick and simple, it is the most operator intensive, and requires extensive training as well as a detailed knowledge of neuroanatomy. Special MRI sequences have been designed to selectively enhance the CSF signal for volume determination, but it is not clear how partial volume averaging is accounted for with those sequences. Moreover, the MRI images generated are not suitable for standard radiological interpretation. Automatic boundary outlining or threshold segmentation routines are usually very time consuming, and require the operator to select "seed" pixel values to start the outlining, or to sample representative pixel intensity values for brain and CSF segmentation.

The present invention provides a simple method of automatically determining an accurate threshold for separating CSF from brain matter signals utilizing any of several T1 weighted MRI images.

DISCLOSURE OF THE INVENTION

It is accordingly one object of the present invention to provide a method of determining regional brain volumes from magnetic resonance images.

Another object of the present invention is to provide a method of determining regional brain volumes and distinguishing between brain and non-brain areas.

A further object of the present invention is to provide a method of analyzing regional volumes in brain structures as they change with healthy aging and brain disease.

A still further object of the present invention is to provide a method of monitoring changes in temporal lobe size in patients with dementia.

According to these and further objects of the present invention which will become apparent as the description thereof is presented below, the present invention provides a method of classifying regional brain volumes which includes the steps of:

a) obtaining a magnetic resonance image of a brain;
 b) loading the magnetic resonance image into a memory of an image processor which includes means for producing a digital image of the magnetic resonance image;
 c) producing a digital image of the magnetic resonance image;
 d) selecting a region of interest of the digital image;
 e) forming a pixel intensity histogram from the region of interest;
 f) dividing the pixel intensity histogram into a plurality of domains;
 g) curve fitting the pixel intensity histogram within the plurality of domains;
 h) determining a threshold pixel intensity from the intersection of the curves produced in step g; and
 i) classifying regional brain volumes based on the threshold pixel intensity.

The present invention further provides a method of monitoring changes in brain structures which comprises the steps of a) obtaining a magnetic resonance image of a brain;
 b) loading the magnetic resonance image into a memory of an image processor which includes means for producing a digital image of the magnetic resonance image;
 c) producing a digital image of the magnetic resonance image;
 d) selecting a region of interest of the digital image;
 e) forming a pixel intensity histogram from the region of interest;
 f) dividing the pixel intensity histogram into a plurality of domains;
 g) curve fitting the pixel intensity histogram within the plurality of domains;
 h) determining a threshold pixel intensity from the intersection of the curves produced in step g; and
 i) classifying regional brain volumes based on the threshold pixel intensity
 j) periodically repeating steps a) through i) at different time periods; and
 k) comparing classified brain volumes determined periodically repeated at different time periods.

BRIEF DESCRIPTION OF DRAWINGS

The present invention will be described with reference to the attached drawings which are given by way of non-limiting examples only, in which.

BEST MODE FOR CARRYING OUT THE INVENTION

The present invention relates to a simple method to accurately and rapidly quantify regional brain, central and subarachnoid CSF volumes from MRI images of human subjects. According to the present invention, which involves pixel intensity distributions using a well behaved mathematical model, parametric statistics can be used to describe various characteristics of the model such as quantitation of partial volume artifact, and threshold weighing schemes. The simplicity of the model enables its use with any image analysis system capable of tracing ROIs on an image and acquiring pixel intensity histograms. In this regard, the method of the present invention can be utilized in cooperation with the image provided by an MRI scanner and thereby allow for immediate on line quantification of brain volumes as opposed to off line analysis. Furthermore, the modelling routine can be applied to any MRI image (including T1 weighted sequences which require less scanning time than the 25 minutes needed for the double echo sequences used here), as long as the image contrast results in at least two identifiable pixel intensity distributions—although its validity on images derived with different MRI sequences and machines needs to be tested.

The present invention involves four procedural steps for the analysis of an MRI image including:

transferring digital image information into the memory of an image analysis system;

tracing regions of interest such as intracranial areas and central CSF spaces on a digital image produced by the image analysis system;

determination of threshold for separation of the image into brain matter and CSF pixels and;

tracing of ROIs for regional brain volumes after threshold had been determined.

A particular feature of the present invention is the fact that the method only requires a single MR image. Moreover, the analysis can be performed on any MR imaging machines, including the more common 0.5 tesla imaging machines.

In practicing the present invention, digital image information is read from an MRI machine and loaded into an image processing system which includes computer memory and conventional image processing hardware.

From the displayed digital images, regions of interest are traced by an operator using known methods, as discussed below. In alternative embodiments, the regions of interest may be determined automatically by the image processing system.

Once the regions of interest are identified a procedure was followed to determine a threshold intensity by which to distinguish and classify image pixels as belonging to a brain. The following steps were used to find the optimal threshold for separation of CSF from brain matter for each ROI:

a pixel intensity histogram was created;

the pixel intensity histogram was smoothed;

a difference histogram was created from the smoothed histogram;

the difference histogram was used to calculate separate pixel domains within the original pixel intensity histogram;

each histogram with each domain was mathematically modelled;

each modelled pixel domain was subtracted from the original matrix to enhance modelling of the remaining domains; and a threshold was determined based on the intersection of two modelled domains.

Features and characteristics of the present invention will be described with reference to the following non-limiting examples which are given for illustrative purposes only.

EXAMPLE 1

Subjects

In this example, temporal lobe and hemispheric volumes were determined for five healthy young and six healthy older subjects. MRIs were analyzed for 5 young adult men with a mean age±standard deviation (sd) of 26±6 years and 6 older men aged 77±4 years. All subjects underwent rigorous medical, neurological and laboratory screening, and had no evidence of cardiovascular, cerebrovascular, or neurological disorders, or a history of drug or alcohol abuse, major psychiatric disorder, or head trauma resulting in unconsciousness.

MRI Protocol

Figure 1A:
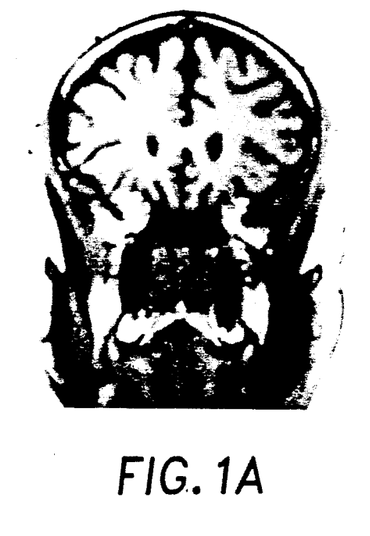
FIG. 1A is the most anterior magnetic resonance image of a human brain on which the middle cranial fossa can be seen.
Figure 1B:
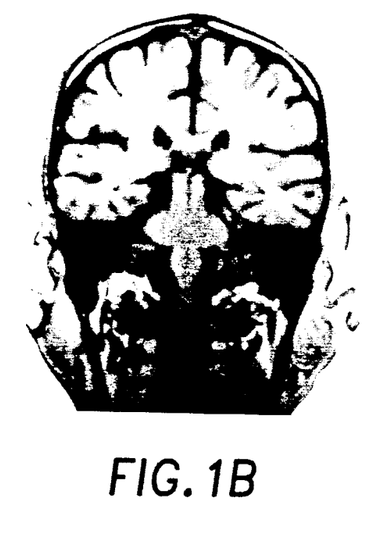
FIG. 1B is the most posterior magnetic resonance image of the human brain of FIG. 1A on which the aqueduct of sylvius could be seen.

MRI was done on a 0.5 Tesla machine (Picker Cleveland, Ohio) using each of two sequences. To determine temporal lobe volume, a spin-echo sequence (TR 500/TE 12) was acquired at 192 views, four repetitions. Sixteen to nineteen, 6 millimeter thick, contiguous slices were obtained in the coronal orientation beginning anterior to the temporal pole and extending past the posterior aspect of the diencephalon (FIG. 1). Image acquisition time was 6.3 minutes per subject. For hemispheric volumes, the T1 weighted (TR 2000 TE 20) portion of a double echo sequence (TR 2000/20/80) was utilized. The double echo sequence, acquired as part of another MRI protocol, was oriented axially and performed with 192 views and two repetitions. Twenty-six to thirty-two, 7-millimeter thick, contiguous slices were obtained from the foramen magnum to the vertex of the brain. Image acquisition time for the double echo sequence was 25 minutes per subject.

Quantitative Analysis

Four major steps were followed in the analysis of each image: (1) LOAD: transfer digital image information onto an image analysis system; (2) TRACE: operating tracing of intracranial areas and central CSF spaces on each image; (3) THRESHOLD: determination of threshold for separation of the image into brain matter and CSF pixels, and; (4) REGIONAL BRAIN VOLUME DETERMINATION: operator tracing of ROIs for regional brain volumes after threshold had been determined.

Load Procedure

Digital image information was read onto tape from the 0.5 Tesla machine and loaded into a memory of an image processing system which included a VAX 11/750 computer (Digital Equipment Corporation, Landover, Md.) and a Gould 8400 image processing hardware (Vicome, Inc., Fairfax, Va.).

Trace Procedure

Figure 2A:
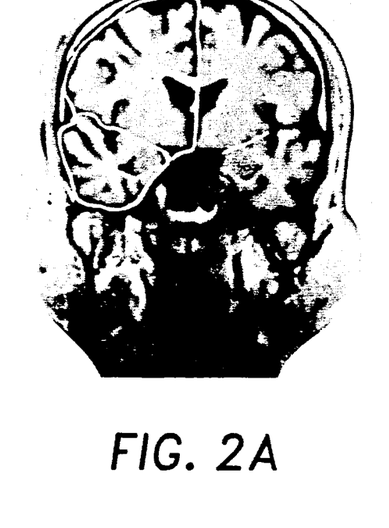
FIG. 2A is the traced region of interest of a temporal lobe of a human brain.
Figure 2B:
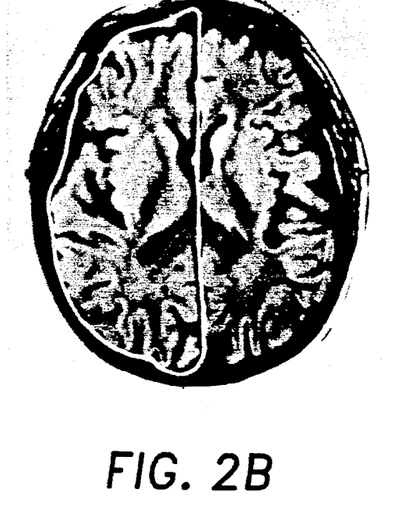
FIG. 2B is the traced region of interest of a hemisphere of a human brain.

The intracranial area and central CSF spaces (which included the third and lateral ventricles) of each eight bit digital image were traced by an operator trained in structural imaging on each slice to be analyzed using the method developed for CT image analysis reported by either DeCarli et al, "Critical Analysis of the Use of Computer-Assisted Transverse Axial Tomography to Study Human Brain in Aging and Dementia of the Alzheimer Type", *Neurology*, Vol. 40 (1990), pages 872-883, or DeLeo et al, "Computer-Assisted Categorization of Brain Computerized Tomography Pixels into Cerebrospinal Fluid, White Matter, and Gray Matter", *Comput. Biomed. Res.*, Vol 18 (1985), pages 79-88, the disclosures of which are expressly incorporated herein by reference. The intracranial ROIs used for calculation of temporal lobe volumes were traced on each MRI slice, extending from the anterior pole of the temporal lobe to the level of the Sylvian aqueduct in the midbrain (FIGS. 1A and 1B). The intracranial area of each MRI slice was outlined by following along the dural surface (FIG. 2A), except over the petrous pyramids, where tracing occurred at the edge of the bone/brain interface. The same method was used for axial images, except that the intracranial ROIs extended from the foramen magnum to the vertex (FIG. 2B).

Threshold Routine

The following steps were used to find the optimal threshold for separation of CSF from brain matter for each intracranial ROI (FIGS. 3A and 3B): (1) create a pixel intensity histogram; (2) smooth the histogram; (3) create a difference histogram from the smoothed histogram; (4) use the difference histogram to calculate separate pixel domains; (5) mathematically model each pixel domain separately; (6) subtract each modelled pixel domain from the original matrix to enhance modelling of the remaining domains; and (7) calculate a threshold based on the intersection of two modelled domains.

Figure 3A:
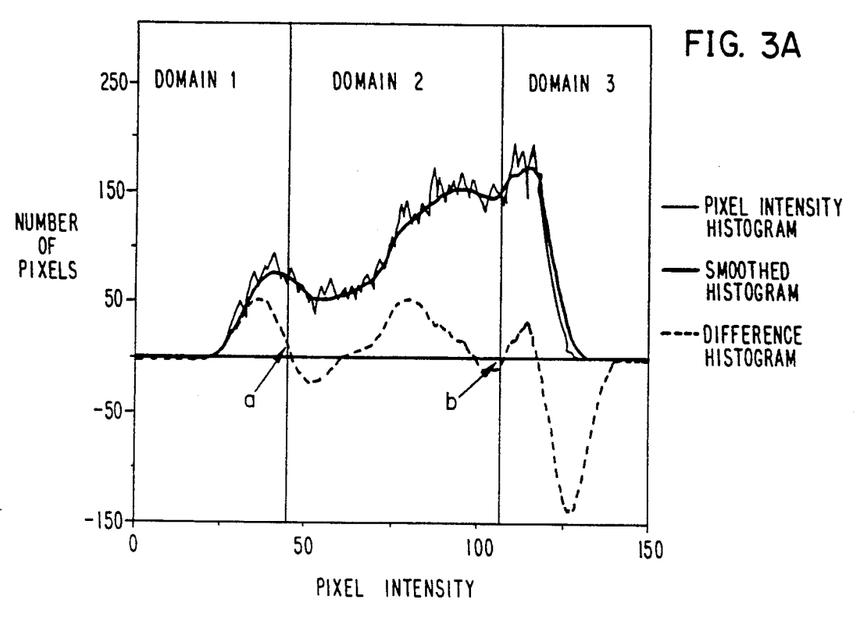
FIG. 3A is a graphic representation of the histogram analysis utilized according to the present invention.
Figure 4A:
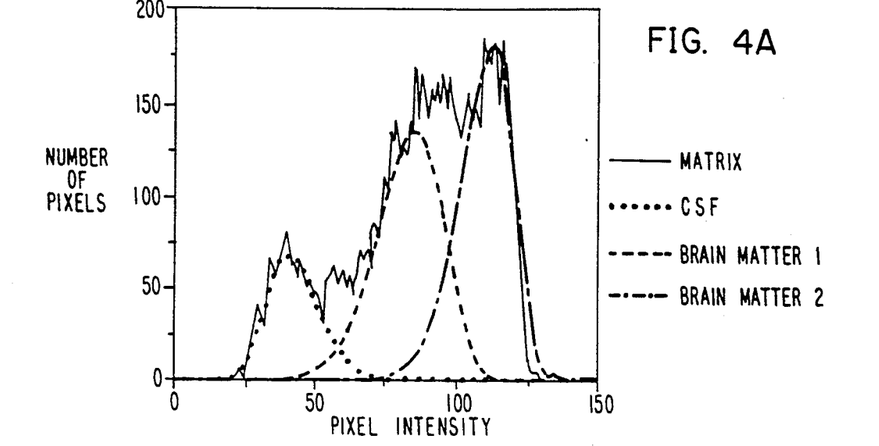
FIGS. 4A–4C are graphic examples of a subtraction method utilized to improve modelling.
Figure 4B:
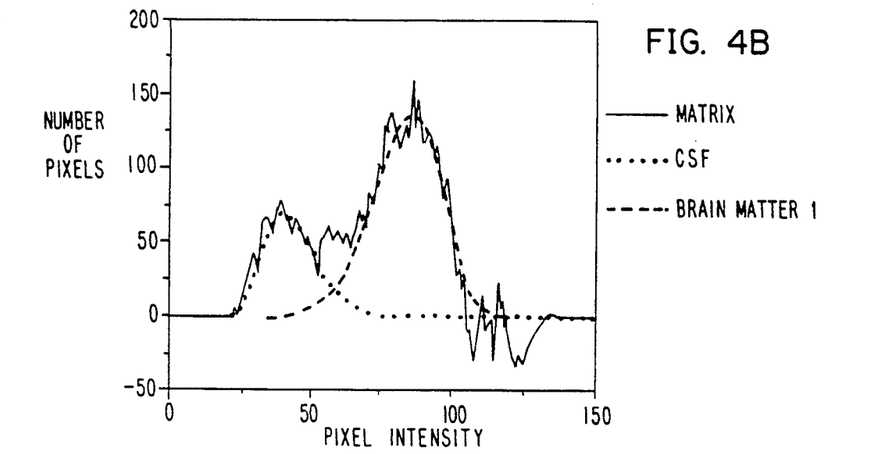
Figure 4C:
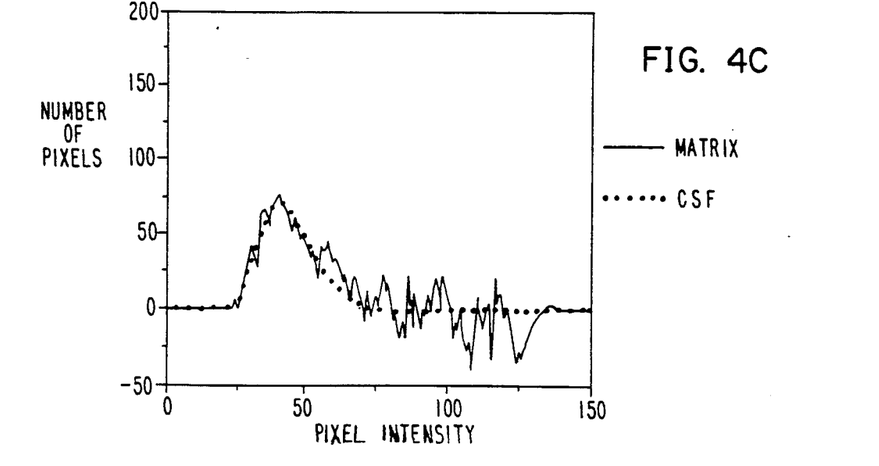

Each pixel intensity histogram was obtained from the digital image information contained within each traced intracranial ROI. Smoothing of the pixel intensity histogram was performed by a sliding mean function which calculated, at each intensity, the mean value of five pixel intensity bins above and below the center pixel intensity bin (FIG. 3A). The difference of the smoothed curve ($D_fx$) then was calculated using the equation $D_fx = f(x_i) - f(x_{i+10})$, where $X_i$ is a given pixel intensity and $f(x_i)$ is the frequency value of the smoothed histogram at pixel intensity $X_i$ (FIG. 3A). Points of inflection along the difference curve were then determined (see italic letters in FIG. 3A). The points of inflection (such as location "a", FIG. 3A) established the limits of each pixel intensity domain mathematically modelled. Finally, a nonlinear least squares algorithm was applied to the segments of the original pixel intensity histogram within each of the domains identified by the difference function. Each domain was modelled separately beginning with the domain of highest mean pixel intensity. After modelling, the pixels described by the modelled function were subtracted from the original pixel histogram to enhance modelling of the remaining pixel domains (FIGS. 4A-4C).

Figure 3B:
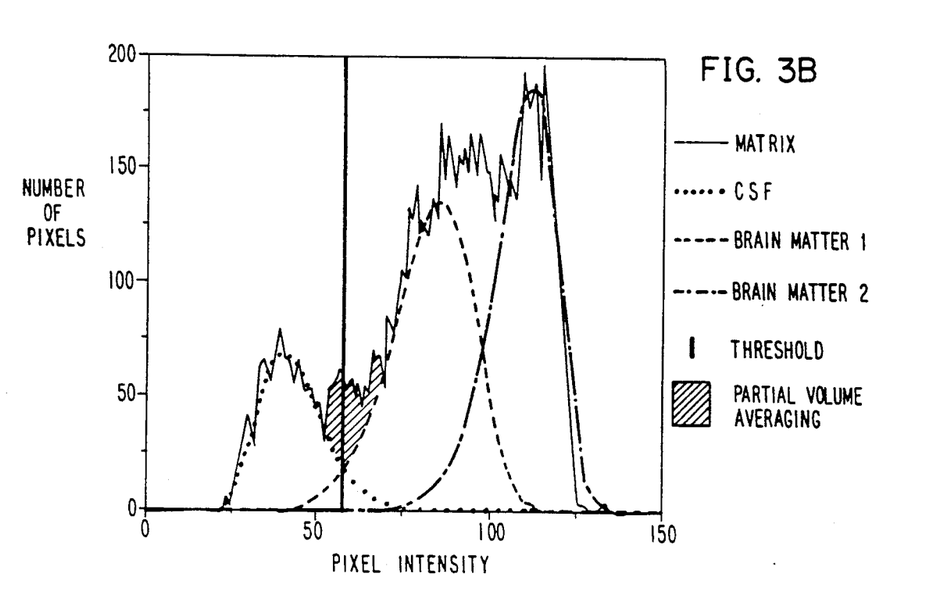
FIG. 3B is a graphic representation of the histogram analysis showing a resultant modelled histogram.

The choice of the nonlinear function was determined to be particularly useful for purposes of the present invention based on empirical observation that a modification of a log normal function best described the pixel distributions to be analyzed. The following modified lognormal equation was used to model MRI pixel distributions:

$$F(x) = \frac{P2}{P3 \sqrt{\pi}} \exp\left[\frac{-(\ln X - P1)^2}{2P3^2}\right]$$

where:
P1 = standard deviation of modelled curve
P2 = peak y value of modelled curve
P3 = x value at mean of modelled curve
$\exp = e^y$
ln = natural log The threshold was taken to be the intersection of modelled pixel distribution of the lowest mean pixel intensity with the nearest pixel distribution (FIG. 3B). Pixels ranging in intensity from 1 to the threshold were counted as CSF, and all pixels with intensity values greater than the threshold were counted as brain matter.

Regional Brain Volume Determination

After segmenting the intracranial area into CSF and brain matter, the operator could return to the original image and outline other ROIs for regional segmentation of CSF from brain matter using the global threshold value. For regional analyses of temporal lobe volumes, the image was divided into four quadrants: the right and left temporal lobes, and the right and left supratemporal quadrants. The medial temporal lobe boundary was defined as a straight line drawn from the angle of the medial temporal lobe where it is attached to the temporal stock, to the midpoint of the operculum (FIG. 2A). The operator then traced the dura of the middle cranial fossa around each temporal lobe to complete the ROI. Similarly, the dura of the supratemporal compartment was traced, dividing the right and left hemisphere by tracing alone the falx cerebri and bisecting the third ventricle, if this structure was present on the image. Only supratentorial structures were analyzed (FIG. 2A).

In the axial orientation, each hemisphere was traced separately by following the dura along the cranial surface. The medial surfaces were bisected by following the dura into the interhemispheric fissure and then drawing a straight line connecting the anterior interhemispheric fissure to the posterior interhemispheric fissure (FIG. 2B).

All trace and threshold volumes were calculated by multiplying the summed pixel areas by the slice thickness. Subarachnoid CSF volumes were calculated by subtracting the sum of the traced central CSF volumes from the regional CSF volume obtained by segmentation (e.g., Right Temporal Subarachnoid CSF Volume ($cm^3$) = Right Temporal CSF Volume ($cm^3$) − Volume of Right Temporal Horn of the Lateral Ventricle Volume ($cm^3$)).

RESULTS

Fittings

Figure 5A:
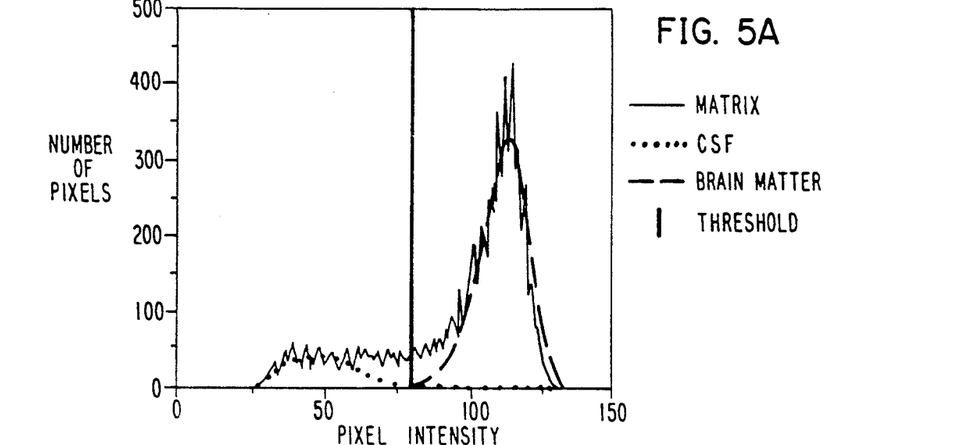
FIGS. 5A–5C are graphic examples of a model fit under various image conditions including a minimal cerebro-spinal fluid space in an image (FIG. 5A), a severe brain atrophy (FIG. 5B), and two brain matter domains (FIG. 5C).
Figure 5B:
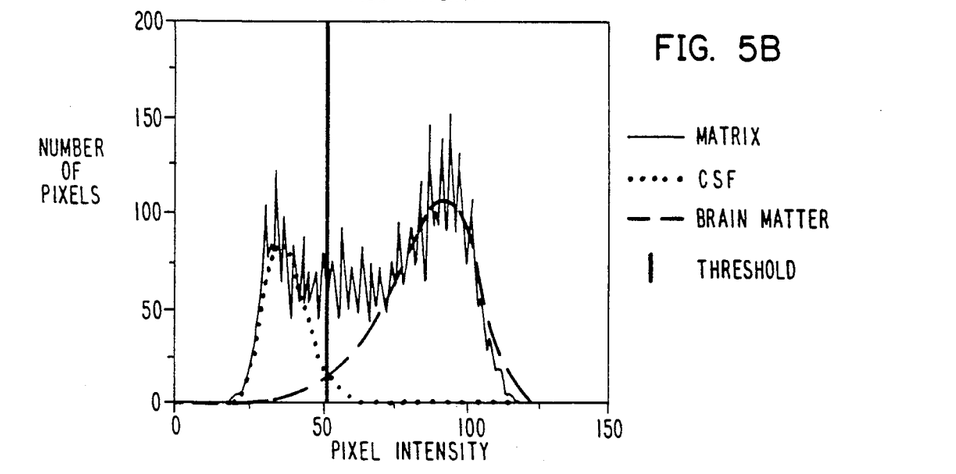
Figure 5C:
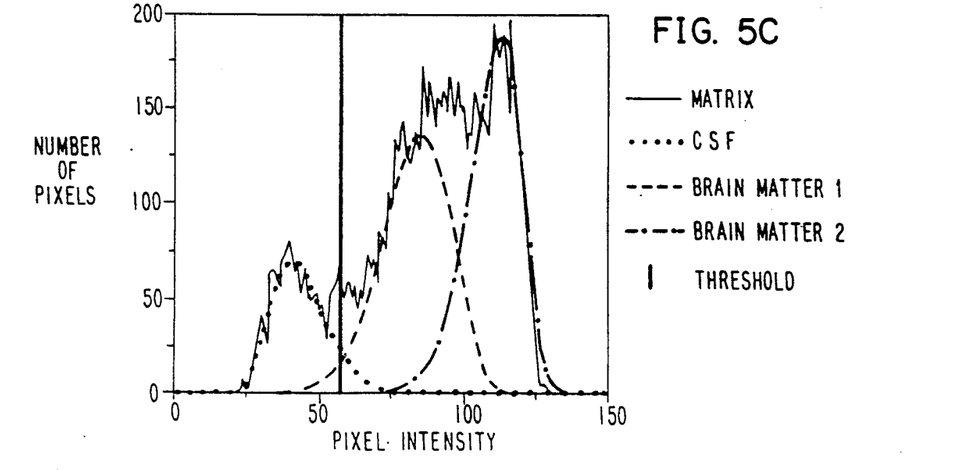

The segmentation routine could be employed over a wide range of conditions, from images with little CSF to images where the majority of pixels were classified as CSF, including images with three distinct pixel distributions (FIGS. 5A–5C). The modelling routine, however, did appear to have a lower limit of approximately 5 percent CSF per slice for a distinct CSF distribution to be calculated (data not shown). In order to compensate for this lower limit, for slices with less than 5 percent CSF, threshold values were calculated as two standard deviations from the mean of the brain matter pixel distribution.

Threshold values, and calculated brain matter and CSF volumes on ten MRI slices could be obtained routinely in 20 minutes. Tracing of central CSF volumes for calculation of subarachnoid CSF and calculation of regional CSF and brain matter volumes required approximately 2 hours to complete.

Figure 2C:
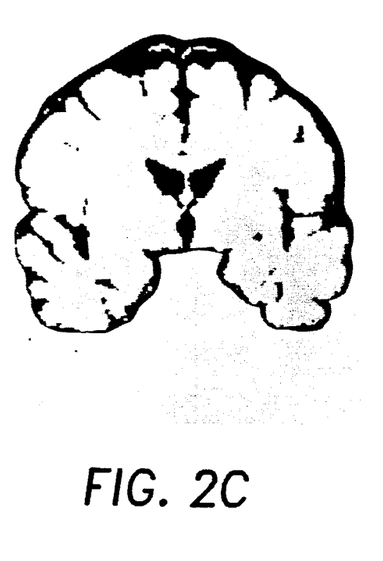
FIGS. 2C and 2D are brain segmentation images which were created from modeling the images of FIGS. 2A and 2B respectively.
Figure 2D:
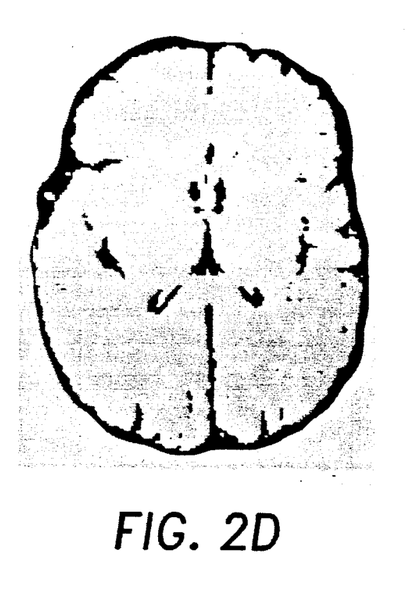

Binary images created from segmentation of brain matter and CSF in the coronal and axial plane are illustrated in FIG. 2C and FIG. 2D.

Effect of Partial Volume Averaging

On average, the modelling routine described $97 \pm 1.3$ (mean$\pm$sd) percent of the variance in total pixels within the image for the young subjects and $94 \pm 1.8$ percent of the variance in total pixels within the image for the older subjects (young vs. older, $p<0.03$). Most of the modelling error occurred in the region of intersection between the pixel populations (FIG. 3B), which is believed to be attributed to partial volume averaging.

The modified lognormal function was designed to account for partial volume averaging by having a skewed distribution. However, it was not certain whether the shape of the distribution resulted in a separation threshold which optimally weighted partial volume effect when the threshold value was defined as the intersection of the two pixel distributions. In an attempt to account for more of the partial volume averaging effect, a weighing scheme which estimated the proportion of CSF and brain matter for each pixel was devised. As part of the weighing scheme, it was assumed that pixel intensities less than the peak pixel intensity in the CSF domain were full volume CSF, whereas pixel intensities greater than the peak intensity in the brain matter domain (assuming 2 pixel populations in this example) were full volume brain matter. This premise was based on the fact that, in general, the tails of the modelled distributions did not go past the peak intensity values of the neighboring distributions FIGS. 4A–4C and 5A–5C). Pixels between the 2 domain peak values were then considered to have a relative proportion of CSF and brain matter as a function of deviation from each modelled distribution, with pixels at the intersection of the two modelled distributions presumed to be 50 percent CSF and 50 percent brain matter. For example, if it is assumed that at an intensity value X, 90 percent of the variance in the pixels is accounted for by the CSF model. By this weighing scheme, 10 percent of the pixels then would be counted as brain matter.

This weighing scheme was applied to determination of intracranial brain and CSF volumes on 10 coronal MRI images. The results of pixel weighing varied less than 1% from those acquired by assuming that pixels at and below the intersection of the two modelled curves were CSF and those above the intersection were brain matter (see Table 1 below). Therefore, the threshold was chosen to be the intersection of the two distributions. Table 1 compares two methods of determining threshold values as discussed above. In Table 1 the number of MRI pixels defined as brain matter is compared for threshold determinations made by simple intersection of modelled distributions or a pixel weighing scheme. Absolute differences are summarized in column 3, whereas the percent differences are summarized in the last column.

TABLE 1

| INTERSECTION METHOD (# PIXELS) | WEIGHTED METHOD (# PIXELS) | ABSOLUTE DIFFERENCE (# PIXELS) | PERCENT DIFFERENCE |
|---|---|---|---|
| 6261 | 6279 | −18 | −0.2 |
| 7958 | 7918 | 40 | 0.5 |
| 8582 | 8615 | −53 | −0.6 |
| 8822 | 8994 | −172 | −2.0 |
| 9999 | 10068 | −69 | −0.6 |
| 10155 | 10281 | −126 | −0.2 |
| 10630 | 10706 | −76 | −0.7 |
| 10646 | 10745 | −99 | −0.9 |
| 10278 | 10408 | −130 | −1.3 |
| 10171 | 10307 | −136 | −1.3 |
| MEAN PERCENT DIFFERENCE | | | −0.8 |

EXAMPLE 2

In this example, the effect of nonuniform RF coil sensitivity on signal intensity was analyzed to determine its effect on the present method.

RF inhomogeneity artifact is a well recognized technical problem of MRI quantitation. Mean pixel intensities vary nonlinearly from one image slice to another, and may vary in intensity within the image. To assess whether the modelling routine could account for changes in image intensity from image slice to image slice within an individual, and for mean changes in image intensity across individuals, the differences in threshold values as a function of slice location within each subject's brain and differences between subject brains was analyzed. Furthermore, threshold values were correlated with pixel intensity values for the peaks of the CSF and brain matter domains determined for each brain slice. Highly significant between subject variance ($F=12.3$, $p<0.0001$) and within subject variance ($F=19.5$, $p<0.0001$) in thresholds were found, suggesting mean changes in MRI signal intensities within the brain image of a single individual, and between individuals. However, threshold determinations did correlate highly with peak CSF pixel intensity values ($r=0.61$, $p<0.0001$) and peak brain matter pixel intensity values ($r=0.71$, $p<0.0001$) suggesting that the modelling routine accounted for slice by slice and intersubject differences in mean pixel intensities.

EXAMPLE 3

In this example, the validity of the present method was tested by measuring temporal lobe volumes from formalin fixed postmortem tissue of the right hemisphere brains of 2 Alzheimer's disease patients. Ringers lactate was used as a substitute for CSF in one comparison, and normal saline solution in the other, as both contain the principle components of CSF. Both hemispheres were imaged according to the temporal lobe protocol described above. After MR imaging, the temporal lobes were dissected from each hemisphere, and the volumes were calculated by displacement of water. The volumes determined by MRI quantification differed from the volumes determined by volume displacement by 1% for both temporal lobes (see Table 2 below) and by 7% for the supratemporal portion of the hemispheres imaged. Table 2 is a comparison of MRI quantification to postmortem volume determined by volume displacement of water. In Table 2 each volume is the mean±sd of five determinations. Hemisphere volumes are the supratemporal portion of the hemisphere on each slice containing temporal lobe. Mean difference denotes the mean of the absolute differences from the postmortem volume determined by volume displacement of water. The brain of patient 1 was submerged in normal saline, whereas the brain of patient 2 was submerged in lactated ringer's solution. R TEM LOBE denotes the right temporal lobe and R HEMISPHERE denotes the right supratemporal portion of the hemisphere.

TABLE 2

| REGION | POST-MORTEM VOLUME ($cm^3$) | CALCULATED MRI VOLUME ($cm^3$) | MEAN DIFFERENCE ($cm^3$) |
|---|---|---|---|
| PATIENT 1 | | | |
| R HEMISPHERE | 217 | 220 ± 21 | 19 ± 4 |
| R TEMP LOBE | 55 | 55 ± 0.7 | 0.6 ± 0.5 |
| PATIENT 2 | | | |
| R HEMISPHERE | 225 | 227 ± 13 | 8 ± 9 |
| R TEMP LOBE | 52 | 52 ± 0.7 | 0.6 ± 0.3 |

Further support for the validity of the present method was determined by comparing results for hemisphere and intracranial volumes to those of postmortem studies. Davis et al, "A New Method for Measuring Cranial Cavity Volume and Its Application to the Assessment of Cerebral Atrophy at Autopsy", *Neuropathol. Appl. Neurobiol.*, Vol. 3 (1977), pages 341-358, reported that the total cranial volume in mean aged 20 years was 1543 $cm^3$ and decreased at 1.77 $cm^3$ per year. Correcting for the mean age of the young group, the predicted cranial volume for the subjects in this study was 1533 $cm^3$. The results were 2 percent larger at 1565±165 $cm^3$ (mean±sd). For the older subjects, the mean total cranial volume was less than 1 percent larger than predicted (1450 $cm^3$ vs. 1443 $cm^3$). Similarly, the hemispheric volumes were 1 percent smaller (621 $cm^3$ vs 628 $cm^3$) than predicted as reported by Miller et al, "Variation with Age in the Volume of Grey and White Matter in the Cerebral Hemispheres of Man: Measurements with an Image Analyser", *Neuropathol. Appl. Neurobiol.*, Vol. 6 (1980), pages 119-132, for the young subjects and 4 percent larger than predicted (534 $cm^3$ vs. 513 $cm^3$) for the older subjects.

Reliability

Intra-rater and inter-rater reliabilities were determined for the 13 ventricular, intracranial and regional ROIs traced by the operators as part of this analysis (Table 3). Highly significant intra-rater and inter-rater reliabilities were obtained for all ROIs.

Brain Volumes

The volumes of all traced ROIs and segmentation results are summarized in Table 3 below. Traced volumes of central CSF spaces, and intracranial volumes did not differ significantly with age, whereas regional brain volumes, determined by the segmentation procedure, differed significantly with age even in this small sample. Table 3 compares regional volumes and reliabilities of the results for young and older subjects. Cranial and ventricular volumes were traced by hand and inter-rater reliabilities were calculated. P-values were student t tested. NS denotes not significant. Reliabilities are expressed as F values. All are significant; however, F values greater than 100 were recorded as 100. Total cranial volume includes all structures within the crainium, whereas cerebrum includes only the hemispheric brain volumes. Temp=temporal; R LAT VENT means right lateral ventricle; L LAT VENT means left lateral ventricle; THIRD VENT means third ventricle; R TEMP HORN means right temporal horn of lateral ventricle; L TEMP HORN means left temporal horn of lateral ventricle.

TABLE 3

| | GROUP | | | RELIABILITY[2] | |
|---|---|---|---|---|---|
| REGION | YOUNG | OLDER | P VALUE[1] | INTER-RATER | INTRA-RATER |
| CRANIAL VOLUMES | | | | | |
| TOTAL CRANIAL[3] | 1565 ± 165 | 1450 ± 134 | NS | 47 | 7 |
| CEREBRUM[3] | 1385 ± 162 | 1292 ± 127 | NS | | |
| R HEMISPHERE | 686 ± 81 | 628 ± 37 | NS | 19 | 5 |
| L HEMISPHERE | 695 ± 82 | 631 ± 25 | NS | 25 | 8 |
| R TEMP LOBE | 88 ± 5 | 79 ± 7 | NS | 14 | 2.4 |
| L TEMP LOBE | 83 ± 9 | 77 ± 9 | NS | 8 | 10 |
| VENTRICULAR VOLUMES | | | | | |
| R LAT VENT | 6.2 ± 2.8 | 11.9 ± 10.5 | NS | 100 | 100 |
| L LAT VENT | 7.2 ± 3.5 | 12.0 ± 10.0 | NS | 46 | 100 |
| THIRD VENT | 1.1 ± 0.5 | 1.3 ± 0.9 | NS | 68 | 100 |
| L TEMP HORN | 0.06 ± 0.06 | 0.7 ± 0.9 | NS | 97 | 100 |
| R TEMP HORN | 0.1 ± 0.03 | 0.7 ± 0.9 | NS | 8 | 11 |
| BRAIN VOLUMES | | | | | |
| TOTAL CEREBRUM | 1243 ± 104 | 1080 ± 119 | 0.04 | | 19 |
| R HEMISPHERE | 621 ± 55 | 534 ± 35 | 0.01 | | 10 |
| L HEMISPHERE | 621 ± 51 | 543 ± 53 | 0.04 | | 26 |
| R TEMP LOBE | 77 ± 6 | 63 ± 6 | 0.004 | | 9 |

TABLE 3-continued

| REGION | GROUP YOUNG | GROUP OLDER | P VALUE[1] | RELIABILITY[2] INTER-RATER | RELIABILITY[2] INTRA-RATER |
|---|---|---|---|---|---|
| L TEMP LOBE | 73 ± 9 | 59 ± 6 | 0.01 | | 14 |
| CSF VOLUMES | | | | | |
| TOTAL CEREBRUM | 141 ± 62 | 198 ± 65 | NS | | 17 |
| R HEMISPHERE | 65 ± 28 | 94 ± 34 | NS | | 17 |
| L HEMISPHERE | 74 ± 32 | 102 ± 30 | NS | | 18 |
| R TEMP LOBE | 11 ± 5 | 16 ± 7 | NS | | 11 |
| L TEMP LOBE | 10 ± 4 | 14 ± 6 | NS | | 17 |
| SUBARACHNOID CSF VOLUMES | | | | | |
| TOTAL CEREBRUM | 127 ± 56 | 187 ± 69 | NS | | 3 |
| R HEMISPHERE | 59 ± 25 | 81 ± 26 | NS | | 8 |
| L HEMISPHERE | 66 ± 29 | 89 ± 21 | NS | | 8 |
| R TEMP LOBE | 12 ± 5 | 15 ± 6 | NS | | 8 |
| L TEMP LOBE | 10 ± 4 | 14 ± 6 | NS | | 13 |

Although the exact effect of RF inhomogeneity on segmentation of MRI images into brain matter and CSF is unknown, it is low in spatial frequency, and may have little effect on volume determination when the segmentation is limited to distinguishing CSF from brain matter. During the course of the present invention it was determined that RF inhomogeneity appears to broaden the brain matter pixel distribution, resulting in a general underestimation of CSF volumes. The effect also appears to be more prominent with images of longer TR duration, as illustrated in FIGS. 2B and 2D. In addition to apparently decreasing CSF volumes, RF inhomogeneities are nonuniform, and appear to increase subject measurement variance. Despite these limitations, however, the segmentation method of the present invention proved to be more sensitive, than manual tracing of the central CSF spaces, to group differences when evaluating age-related differences in a small group of subjects. Further support for the accuracy of the present method is found in the similarity between results such as those presented herein, postmortem quantitation of the same regions, and the results of Tanna et al, "Analysis of Brain and Cerebrospinal Fluid Volumes with MRI Imaging: Impact on PET Data Correction for Atrophy", *Radiology*, Vol. 178 (1991), pages 128–130, using the 2D histogram method.

The mean temporal lobe volumes reported herein were larger than those obtained using other MRI quantitation methods, but smaller on a percent basis than postmortem quantitation. The disparity between these findings likely reflects differences in choice of temporal lobe boundaries. For purposes of reliability in the present disclosure, medial temporal lobe boundaries were drawn from the medial basal angle of the temporal lobe to bisect the base of the opercular triangle (FIG. 2), whereas others have drawn the medial border as a straight line across the isthmus of the temporal lobe stalk. Moreover, the posterior temporal lobe boundary used in the above example was at least 6 millimeters caudal to the posterior boundary of other methods. However, despite the generous boundaries used, inferior caudal portions of the temporal lobe are excluded. In postmortem quantification, landmarks can be more easily identified. The inferior caudal portions of the temporal lobes may have been included in quantification of temporal lobe volume in the postmortem study resulting in a larger proportion of intracranial volume. Results of MRI quantification of temporal lobe volumes, therefore, must be placed in perspective according to the boundaries used to identify this complex shaped structure.

Although the present invention has been described with reference to particular means, materials and embodiments, from the foregoing description, one skilled in the art can easily ascertain the essential characteristics of the present invention and various changes and modifications may be made to adapt the various uses and characteristics without departing from the spirit and scope of the present invention as described by the claims that follow.

What is claimed is:

1. A method of classifying regional brain volumes which comprises the steps of:
    a) obtaining a magnetic resonance image of a brain;
    b) loading said magnetic resonance image into a memory of an image processor which includes means for producing a digital image of said magnetic resonance image;
    c) producing a digital image of said magnetic resonance image;
    d) selecting a region of interest of said digital image;
    e) forming a pixel intensity histogram from said region of interest;
    f) dividing said pixel intensity histogram into a plurality of domains;
    g) curve fitting said pixel intensity histogram within said plurality of domains;
    h) determining a threshold pixel intensity from the intersection of the curves produced in step g; and
    i) classifying regional brain volumes based on said threshold pixel intensity.

2. A method of classifying regional brain volumes according to claim 1, wherein said magnetic resonance image comprises a T1 weighted magnetic resonance image.

3. A method of classifying regional brain volumes according to claim 1, wherein said selection of a region of interest comprises tracing a region of interest of said digital image.

4. A method of classifying regional brain volumes according to claim 1, wherein said loading of said magnetic resonance image into an image processor comprises scanning said magnetic resonance image.

5. A method of classifying regional brain volumes according to claim 2, wherein said magnetic resonance image is produced at 0.5 Tesla.

6. A method of monitoring changes in brain structures which comprises the steps of a) obtaining a magnetic resonance image of a brain;
b) loading said magnetic resonance image into a memory of an image processor which includes means for producing a digital image of said magnetic resonance image;
c) producing a digital image of said magnetic resonance image;
d) selecting a region of interest of said digital image;
e) forming a pixel intensity histogram from said region of interest;
f) dividing said pixel intensity histogram into a plurality of domains;
g) curve fitting said pixel intensity histogram within said plurality of domains;
h) determining a threshold pixel intensity from the intersection of the curves produced in step g; and
i) classifying regional brain volumes based on said threshold pixel intensity j) periodically repeating steps a) through i) at different time periods; and
k) comparing classified brain volumes determined periodically repeated at different time periods.

7. A method of classifying regional brain volumes according to claim 5, wherein said magnetic resonance image comprises a T1 weighted magnetic resonance image.

8. A method of classifying regional brain volumes according to claim 5, wherein said selection of a region of interest comprises tracing a region of interest of said digital image.

9. A method of classifying regional brain volumes according to claim 5, wherein said loading of said magnetic resonance image into an image processor comprises scanning said magnetic resonance image.

10. A method of classifying regional brain volumes according to claim 7, wherein said magnetic resonance image is produced at 0.5 Tesla.

* * * * *